United States Patent
Brackhagen et al.

(10) Patent No.: US 9,745,387 B2
(45) Date of Patent: Aug. 29, 2017

(54) PARTIALLY CROSS-LINKED ESTERIFIED CELLULOSE ETHERS

(71) Applicant: Dow Global Technologies LLC, Midland, MI (US)

(72) Inventors: Meinolf Brackhagen, Walsrode (DE); Nicholas S. Grasman, Midland, MI (US); Yongfu Li, Midland, MI (US); David M. Meunier, Midland, MI (US); Oliver Petermann, Hamburg (DE); Matthias Sprehe, Walsrode (DE)

(73) Assignee: Dow Global Technologies LLC

( * ) Notice: Subject to any disclaimer, the term of this patent is extended or adjusted under 35 U.S.C. 154(b) by 107 days.

(21) Appl. No.: 14/420,985

(22) PCT Filed: Aug. 15, 2013

(86) PCT No.: PCT/US2013/055037
§ 371 (c)(1),
(2) Date: Feb. 11, 2015

(87) PCT Pub. No.: WO2014/031418
PCT Pub. Date: Feb. 27, 2014

(65) Prior Publication Data
US 2015/0203597 A1    Jul. 23, 2015

Related U.S. Application Data

(60) Provisional application No. 61/692,927, filed on Aug. 24, 2012.

(51) Int. Cl.
| | | |
|---|---|---|
| *C08B 13/00* | (2006.01) | |
| *C08B 11/20* | (2006.01) | |
| *A61K 9/10* | (2006.01) | |
| *A61K 9/28* | (2006.01) | |
| *A61K 9/14* | (2006.01) | |

(52) U.S. Cl.
CPC .............. *C08B 13/00* (2013.01); *A61K 9/10* (2013.01); *A61K 9/2866* (2013.01); *C08B 11/20* (2013.01); *A61K 9/146* (2013.01)

(58) Field of Classification Search
None
See application file for complete search history.

(56) References Cited

U.S. PATENT DOCUMENTS

| | | |
|---|---|---|
| 4,226,981 A | 10/1980 | Onda et al. |
| 4,316,982 A | 2/1982 | Holst et al. |
| 4,365,060 A | 12/1982 | Onda et al. |
| 5,776,501 A | 7/1998 | Kokubo et al. |

FOREIGN PATENT DOCUMENTS

| | | |
|---|---|---|
| EP | 0210917 | 2/1987 |
| EP | 0219426 A2 | 4/1987 |
| EP | 0872233 | 10/1998 |
| EP | 1141029 | 10/2001 |
| EP | 1423433 B1 | 6/2004 |
| WO | 02085949 A1 | 10/2002 |
| WO | 2005115330 A2 | 12/2005 |
| WO | 2006082518 A1 | 8/2006 |
| WO | 2011159626 A1 | 12/2011 |

OTHER PUBLICATIONS

Chen et al.; J. Pharmaceutical and Biomedical Analysis; 56(2011); pp. 743-748 (pub'd online Jul. 30, 2011).*
Drugs and the Pharma. Sciences, 1997, pp. 385-418, Aqueous Polymeric Coatings, Wu et al.
Cellulose, 2007, pp. 49-64, Cellulose esters in drug delivery, Edgar.
Int. Journal of Polymer Anal.Charact., 14, 2009, pp. 617-630, Characerization of Hypromellose Acetate Succinate, Chen.
Europ. Journal of Pharma. and Biopharma., 54, 2002, pp. 107-117, Melt extrusion, Breitenbach.
Carbohydrate Polymers, 45, 2001, pp. 293-303, Characterization of Methocel, Keary.

* cited by examiner

*Primary Examiner* — Jeffrey T Palenik

(57) ABSTRACT

A partially cross-linked esterified cellulose ether having A) groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation, and B) having a molecular weight distribution such that [Wf(>100 k)−Wf(>100 k)XL]/Wf(>100 k)XL is at least 0.20, wherein Wf(>100 k) is the total weight fraction of the esterified cellulose ether that exceeds 100,000 g/mol, and Wf(>100 k)XL is the weight fraction that exceeds 100,000 g/mol of the methylated esterified cellulose ether is useful as enteric polymer for pharmaceutical dosage forms.

15 Claims, No Drawings

PARTIALLY CROSS-LINKED ESTERIFIED CELLULOSE ETHERS

FIELD

This invention concerns novel esterified cellulose ethers, solid dispersions of an active ingredient in such esterified cellulose ether, as well as liquid compositions, coated dosage forms and capsules comprising such esterified cellulose ether.

INTRODUCTION

Esters of cellulose ethers, their uses and processes for preparing them are generally known in the art. Various known esterified cellulose ethers are useful as enteric polymers for pharmaceutical dosage forms, such as hydroxypropyl methyl cellulose acetate succinate (HPMCAS). Enteric polymers are those that are resistant to dissolution in the acidic environment of the stomach. Dosage forms coated with such polymers protect the drug from inactivation or degradation in the acidic environment or prevent irritation of the stomach by the drug.

U.S. Pat. No. 4,365,060 discloses enterosoluble capsules which are said to have excellent enterosolubility behavior. The enterosoluble capsules are shaped with an ester of a cellulose ether that is esterified with acidic succinyl groups and aliphatic monovalent acyl groups. It is recommended that the cellulose ethers used for esterification have a molecular weight in the range from about 5000 to 200,000 to obtain adequate plasticity.

Wu et al. (Wu S. H. W., Wyatt D. M. and Adams M. W. 1997; *Chemistry and applications of cellulosic polymers for enteric coatings of solid dosage forms*; in McGinity J. W. (ed.), *Aqueous Coatings for Pharmaceutical Dosage Forms*, Marcel Dekker, New York, pp. 385-418) disclose molecular weights of commercially available different grades of HPMCAS. HPMCAS grade AS-L has an $M_w$ of 93,000, an $M_n$ of 46,000 (both measured by gel permeation chromatography method calibrated by polyethylene oxide) and an $M_w/M_n$ of 2.0; HPMCAS grade AS-M has an $M_w$ of 80,000, an $M_n$ of 44,000 and an $M_w/M_n$ of 1.8; and HPMCAS grade AS-H has an $M_w$ of 55,000 an $M_n$ of 33,000 and an $M_w/M_n$ of 1.7.

U.S. Pat. No. 4,226,981 discloses a process for preparing mixed esters of cellulose ethers, such as hydroxypropyl methyl cellulose acetate succinate (HPMCAS), by esterifying hydroxypropyl methylcellulose with succinic anhydride and acetic anhydride in the presence of an alkali carboxylate as the esterification catalyst and acetic acid as the reaction medium. The cellulose ether as the base material is introduced into the reaction vessel together with about 100 to 2,000 parts by weight of the carboxylic acid as the reaction medium and about 20 to 200 parts by weight of the alkali carboxylate as the catalyst, all being expressed per 100 parts by weight of the cellulose ether, followed by further introduction of predetermined amounts of succinic anhydride and an anhydride of an aliphatic monocarboxylic acid, the resulting mixture being heated at 60 to 110° C. for a period of 2-25 hours. In the working examples 250 g of acetic acid and 50 g of sodium acetate are utilized per 50 g of hydroxypropyl methyl cellulose. 15-60 g of succinic anhydride and 25-80 g of acetic anhydride are added and the reaction mixture is heated at 85° C. with agitation for 3 hours.

European Patent Application EP 0 219 426 discloses a process for producing an enteric-soluble acidic dicarboxylic acid ester of a cellulose ether wherein (a) a cellulose ether having hydroxypropoxyl groups as the ether-forming groups, of which a 2% by weight aqueous solution has a viscosity of at least 5 centipoise at 20° C., is reacted with (b) a dicarboxylic acid anhydride or a mixture thereof with an anhydride of an aliphatic monocarboxylic acid in the presence of (c) a combination of an alkali metal acetate and acetic acid. EP 0 219 426 shows that the acidic dicarboxylic acid esters produced from cellulose ethers which have a viscosity of at least 6 centipoise provided an enterosoluble film-coating material on tablets which had resistance against a simulated gastric juice. When comparative acidic dicarboxylic acid esters were produced from cellulose ethers having a viscosity of only 3 centipoise, a substantial number of tablets disintegrated in the simulated gastric juice. Acidic dicarboxylic acid esters produced from cellulose ethers of higher viscosity have a higher molecular weight than those produced from cellulose ethers of lower viscosity when comparable process and recipe parameters for producing the acidic dicarboxylic acid esters are applied.

A large number of presently known drugs have a low solubility in water, and thus complex techniques are required to prepare a dosage form. One known method includes dissolving such drug together with a pharmaceutically acceptable water-soluble polymer in an organic solvent that is optionally blended with water, and to spray-dry the solution. Another method is known as melt extrusion, wherein a drug is blended with a pharmaceutically acceptable water-soluble polymer as a powder blend, the powder blend is heated and intensely mixed in the softened or partially or completely melted state and moved towards a die that shapes the melt as strands, films, pellets, tablets or capsules. The pharmaceutically acceptable water-soluble polymer is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

International Patent Application WO 2005/115330 discloses hydroxypropyl methyl cellulose acetate (HPMCA) polymers and hydroxypropyl methyl cellulose acetate succinate (HPMCAS) polymers with a specific combination of substitution levels. The HPMCAS polymer has a degree of substitution of succinoyl groups ($DOS_S$) of at least 0.02, a degree of substitution of acetyl groups ($DOS_{Ac}$) of at least 0.65 and a sum of $DOS_{Ac}$ and $DOS_S$ of at least 0.85. The HPMCA polymer has a degree of substitution of acetyl groups ($DOS_{Ac}$) on said HPMPA of at least 0.15. WO 2005/115330 discloses that the increased acetate substitution allows increased solubility of active agents in spray-dried solutions, while the increased succinate substitution increases the solubility of the polymer in aqueous solution.

International Patent Application WO 2011/159626 discloses an active ingredient and HPMCAS having a degree of substitution of methoxy groups ($DS_M$) of ≤1.45, and a combined degree of substitution of acetyl groups ($DS_{Ac}$) and succinoyl groups ($DS_S$) of ($DS_{Ac}+DS_S$)≥1.25.

However, in view of the large diversity of drugs, it is self-evident that a limited variety of esterified cellulose ethers having a high degree of substitution of acetyl groups and succinoyl groups cannot fulfill all needs. Edgar et al., Cellulose (2007), 14:49-64 "Cellulose esters in drug delivery" state in the conclusion of their survey article: "The fundamental properties of cellulose esters are well-suited to improving drug delivery . . . . Much progress has been made in recent years in the application of well-studied cellulose esters to improve drug delivery systems. There is room for much more advancement, particularly by the in-depth study of structure property relationships as they pertain to pharmaceutical applications. Full success in this endeavor will require considerable vision, since the current path to market for novel pharmaceutical excipients is difficult, long, fraught with uncertainty, and expensive."

Accordingly, it is one object of the present invention to provide to provide new esterified cellulose ethers. It is known that polymers do not have a singular molecular weight but a distribution of molecular weights. In view of the advantages of the acidic dicarboxylic acid esters of increased molecular weight produced from higher viscosity cellulose ethers as discussed in EP 0 219 426, it is a preferred object of the present invention to provide new esterified cellulose ethers having a polymer weight distribution with a fraction of high molecular weight. On the other hand, if esterified cellulose ethers have a large weight fraction of irreversibly high molecular weight, the esterified cellulose ethers generally have an increased amount of undissolved particles in organic solvents. An increased amount of undissolved particles in organic solvents is undesirable when an esterified cellulose ether is subjected to spray-drying because of an increased tendency to clogging devices used for spray-drying, such as spray nozzles. Moreover, an increased amount of undissolved particles in organic solvents tends to increase the turbidity of the organic solution, which is undesirable when the esterified cellulose ethers are used in transparent films or coatings. Accordingly, it is another preferred object of the present invention to provide new esterified cellulose ethers that do not have an overly large weight fraction of irreversibly high molecular weight.

SUMMARY

One aspect of the present invention is an esterified cellulose ether having
A) groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation, and
B) having a molecular weight distribution such that [Wf(>100 k)−Wf(>100 k)XL]/Wf(>100 k)XL is at least 0.20,
wherein Wf(>100 k) is the total weight fraction of the esterified cellulose ether that exceeds 100,000 g/mol, and Wf(>100 k)XL is the weight fraction that exceeds 100,000 g/mol of the methylated esterified cellulose ether.

Another aspect of the present invention is a composition comprising a liquid diluent and at least one esterified cellulose ether as described above.

Yet another aspect of the present invention is a solid dispersion comprising at least one active ingredient in at least one esterified cellulose ether as described above.

Yet another aspect of the present invention is a process for producing a solid dispersion which comprises the steps of blending a) at least one esterified cellulose ether as described above, b) one or more active ingredients and c) one or more optional additives, and subjecting the blend to extrusion.

Yet another aspect of the present invention is a process for producing a solid dispersion which comprises the steps of blending a) at least one esterified cellulose ether as described above, b) one or more active ingredients, c) one or more optional additives, and d) a liquid diluent to prepare a liquid composition, and removing said liquid diluent.

Yet another aspect of the present invention is a dosage form which is coated with the esterified cellulose ether as described above.

Yet another aspect of the present invention is a capsule shell which comprises the esterified cellulose ether as described above.

DETAILED DESCRIPTION

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.90, more preferably 0.12 to 0.70, most preferably 0.15 to 0.60, and particularly 0.20 to 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention preferably have a DS(alkoxyl) in the range of 1.0 to 2.5, more preferably from 1.1 to 2.4, most preferably from 1.2 to 2.2 and particularly from 1.6 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention has groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation. The cation preferably is an ammonium cation, such as $NH_4^+$ or an alkali metal ion, such as the sodium or potassium ion, more preferably the sodium ion. Most preferably, A is hydrogen.

The aliphatic monovalent acyl groups are preferably selected from the group consisting of acetyl, propionyl, and butyryl, such as n-butyryl or i-butyryl.

Preferred groups of the formula —C(O)—R—COOA are —C(O)—CH$_2$—CH$_2$—COOA, such as —C(O)—CH$_2$—CH$_2$—COOH or —C(O)—CH$_2$—CH$_2$—COO$^-$Na$^+$, —C(O)—CH=CH—COOA, such as —C(O)—CH=CH—COOH or —C(O)—CH=CH—COO$^-$Na$^+$, or —C(O)—C$_6$H$_4$—COOA, such as —C(O)—C$_6$H$_4$—COOH or —C(O)—C$_6$H$_4$—COO$^-$Na$^+$.

In the groups of formula —C(O)—C$_6$H$_4$—COOA the carbonyl group and the carboxylic group are preferably arranged in ortho-positions.

Preferred esterified cellulose ethers are i) HPMCXY, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), or hydroxypropyl methylcellulose acetate succinate (HPMCAS), or ii) hydroxypropyl methyl cellulose phthalate (HPMCP), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of 0 to 1.75, preferably of 0.05 to 1.50, more preferably of 0.10 to 1.25, and most preferably of 0.20 to 1.00.

The esterified cellulose ethers generally have a degree of substitution of groups of formula —C(O)—R—COOA, such as succinoyl, of 0.05 to 1.6, preferably of 0.05 to 1.30, more preferably of 0.05 to 1.00, and most preferably of 0.10 to 0.70 or even 0.10 to 0.60.

The sum of i) the degree of substitution of aliphatic monovalent acyl groups and ii) the degree of substitution of groups of formula —C(O)—R—COOA is generally from 0.05 to 2.0, preferably from 0.10 to 1.4, more preferably from 0.20 to 1.15, most preferably from 0.30 to 1.10 and particularly from 0.40 to 1.00.

The content of the acetate and succinate ester groups is determined according to "Hypromellose Acetate Succinate", United States Pharmacopia and National Formulary, NF 29, pp. 1548-1550. Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) - \left(\% \text{ HPO} * \frac{M(OCH_2CH(OH)CH_3) - M(OH)}{M(OCH_2CH(OH)CH_3)}\right) - \left(\% \text{ Acetyl} * \frac{M(COCH_3) - M(H)}{M(COCH_3)}\right) - \left(\% \text{ Succinoyl} * \frac{M(COC_2H_4COOH) - M(H)}{M(COC_2H_4COOH)}\right)$$

$$DS(Me) = \frac{\frac{\% \text{MeO}}{M(OCH_3)}}{\frac{\% \text{ cellulose backbone}}{M(AGU)}}$$

$$MS(HP) = \frac{\frac{\% \text{ HPO}}{M(HPO)}}{\frac{\% \text{ cellulose backbone}}{M(AGU)}}$$

$$DS(Acetyl) = \frac{\frac{\% \text{ Acetyl}}{M(Acetyl)}}{\frac{\% \text{ cellulose backbone}}{M(AGU)}}$$

$$DS(Succinoyl) = \frac{\frac{\% \text{ Succinoyl}}{M(Succinoyl)}}{\frac{\% \text{ cellulose backbone}}{M(AGU)}}$$

$M(MeO) = M(OCH_3) = 31.03 \ Da$ $M(HPO) = M(OCH_2CH(OH)CH_3) = 75.09 \ Da$ $M(Acetyl) = M(COCH_3) = 43.04 \ Da$ $M(Succinoyl) = M(COC_2H_4COOH) = 101.08 \ Da$ $M(AGU) = 162.14 \ Da$ $M(OH) = 17.008 \ Da$ $M(H) = 1.008 \ Da$ By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O— alkylene-OH); such as hydroxypropoxyl (i.e., —O—$CH_2CH(CH_3)$—OH). The content of the aliphatic monovalent acyl groups is reported based on the mass of —C(O)—$R_1$ wherein $R_1$ is a monovalent aliphatic group, such as acetyl (—C(O)—$CH_3$). The content of the group of formula —C(O)—R—COOH is reported based on the mass of this group, such as the mass of succinoyl groups (i.e., —C(O)—$CH_2$—$CH_2$—COOH).

The esterified cellulose ethers of the present invention are unique in that they have a [Wf(>100 k)–Wf(>100 k)XL]/Wf(>100 k)XL that is at least 0.20,
wherein Wf(>100 k) is the total weight fraction of the esterified cellulose ether that exceeds 100,000 g/mol, and Wf(>100 k)XL is the weight fraction that exceeds 100,000 g/mol of the methylated esterified cellulose ether.

Wf(>100 k), i.e, the total weight fraction of the esterified cellulose ether that exceeds 100,000 g/mol, is determined by Size Exclusion Chromatography (SEC) using tetrahydrofuran (THF) as eluent and polystyrene calibration standards. The weight fraction that exceeds 100,000 g/mol of the methylated esterified cellulose ether, Wf(>100 k)XL, is determined via characterization of the methylated esterified cellulose ether by Size Exclusion Chromatography (SEC) using tetrahydrofuran (THF) as eluent and polystyrene calibration standards and by determining the weight fraction that exceeds 100,000 g/mol of the methylated esterified cellulose ether. The term "methylated esterified cellulose ether" as used herein means an esterified cellulose ether that has been subjected to a further methylation reaction, i.e., after the production of the esterified cellulose ether for analytical purposes to determine Wf(>100 k)XL. To avoid any doubts, the terms "methylated" esterified cellulose ether and "methylation" of the esterified cellulose ether do not refer to a methylation reaction that is carried out to produce the esterified cellulose ether. The terms "methylated" and "methylation" refer to a further methylation reaction that is conducted on a given esterified cellulose ether, such as an esterified cellulose ether of the present invention or another esterified cellulose ether to be analyzed. The methods for methylating the esterified cellulose ether and for determining the weight fraction that exceeds 100,000 g/mol are described in more details in the Examples section.

In cases where esterified cellulose ethers are produced from cellulose ethers which have a weight-average molecular weight of about 100,000 g/mol or more, as determined by Size Exclusion Chromatography (SEC), the esterified cellulose ether has a high fraction of linear esterified cellulose ether chains that have a molecular weight of more than 100,000 g/mol. In this case Wf(>100 k); i.e., the total weight fraction of the esterified cellulose ether that exceeds 100,000 g/mol, and Wf(>100 k)XL, i.e., the weight fraction that exceeds 100,000 g/mol of the methylated esterified cellulose ether, are substantially the same and [Wf(>100 k)–Wf(>100 k)XL] is close to zero, as explained in more details below.

It is known in the art that esterified cellulose ethers can have higher molecular weights than would be expected based on the molecular weights of the cellulose ethers used as a starting material and the weight gain by the esterification reaction(s). For example, a cellulose ether that has a viscosity of 3 mPa·s, 5 mPa·s, and 15 mPa·s respectively, measured as a 2 weight-% aqueous solution at 20° C. according to ASTM D2363-79 (Reapproved 2006), has a weight average molecular weight of about 20000 g/mol, about 30000 g/mol, and about 60000 g/mol respectively [C. Keary, *Carbohydrate Polymers* 45 (2001) 293-303].

R. Chen, *International Journal of Polymer Anal. Charact.* 14: 617-630, 2009, "Characterization of Hypromellose Acetate Succinate by Size Exclusion Chromatography (SEC) Using Viscotek Triple Detector", discusses that the $M_w$ values or Hypromellose Acetate Succinate (HPMCAS) polymers are at least several multiples higher than the values of corresponding hydrolyzed HPMCAS polymers. Chen theorizes that both acetyl and succinoyl groups may not be evenly substituted along the HPMC polymer chains during the esterification process. An unevenly substituted "heterogeneous" HPMCAS polymer chain would behave like block copolymer. The "heterogeneous" HPMCAS polymer chains in solution would form a "shell-core" type aggregation and have the characteristic conformation change from low to high molecular weights. Chen states that in the low molecular weight range, the HPMCAS polymer chains are short, have less degree of "hetereogeity" and as a result, the polymer chains are less entangled. Chen theorizes that as the molecular weight increases, the polymer chains will become longer, have a progressively higher degree of "hetereogeity" and as a consequence the polymer chains become increasingly entangled.

Applicants believe that the presence of groups —COOA, wherein A is hydrogen or a cation, in the esterified cellulose ethers facilitates cross-linking, i.e., covalently linking one polymer chain to another, which leads to an increased molecular weight of the polymer chains. Applicants of the present invention have found that the higher than expected molecular weights of the esterified cellulose ethers are not only caused by cross-linking but also by some other interactions of the polymer chains. Without wanting to be bound by the theory, Applicants believe that such other interactions are chain association or chain aggregation.

Applicants have found that high molecular weight fractions of an esterified cellulose ether caused by other interactions of the polymer chains than by chain cross-linking can be determined by methylating the —COOA groups of the esterified cellulose ether and measuring the total weight fraction that exceeds 100,000 g/mol of the methylated esterified cellulose ether, in addition to measuring the total weight fraction that exceeds 100,000 g/mol of the non-methylated esterified cellulose ether (i.e., an esterified cellulose ether that has not undergone a further methylation reaction).

The total weight fraction that exceeds 100,000 g/mol of the non-methylated esterified cellulose ether (i.e., an esterified cellulose ether that has not undergone a further methylation reaction), Wf(>100 k), is caused by i) linear polymer chains, ii) cross-linked polymer chains whose interaction is not reversible by methylation of the —COOA groups and iii) by interactions of polymer chains that are reversible upon methylation of the —COOA groups, i.e. that disappear upon methylation of the —COOA groups, such as chain association and/or chain aggregation. Wf(>100 k) preferably is 15 percent or more, more preferably 20 percent or more, and most preferably 23 percent or more, based on the total weight of the esterified cellulose ether. Wf(>100 k) preferably is 50 percent or less, more preferably 45 percent or less, and most preferably 37 percent or less, based on the total weight of the esterified cellulose ether.

The weight fraction that exceeds 100,000 g/mol of the methylated esterified cellulose ether, Wf(>100 k)XL, is caused by i) linear polymer chains and ii) cross-linked polymer chains whose interaction is not reversible by methylation of the —COOA groups. Conversion of the COOA groups to their methyl esters eliminates chain interactions such as chain association and/or chain aggregation caused by the COOA groups, but conversion of the COOA groups to their methyl esters does not eliminate chain cross-linking.

Depending on the weight average molecular weight of the cellulose ether that is used for producing the esterified cellulose ether, the weight fraction that exceeds 100,000 g/mol caused by linear polymer chains is small, and in some cases can even be neglected, as compared to the weight fraction caused by cross-linked polymer chains. This is the case, e.g., when using a cellulose ether that has a viscosity of up to 5 mPa·s, measured as a 2 weight-% aqueous solution at 20° C. according to ASTM D2363-79 (Reapproved 2006).

The difference [Wf(>100 k)−Wf(>100 k)XL] is caused by interactions of polymer chains that are reversible upon methylation of the —COOA groups, i.e. that disappear upon methylation of the —COOA groups. Exemplary of interactions of polymer chains that are reversible upon methylation of the —COOA groups are chain association and/or chain aggregation. Without wanting to be bound to the theory, applicants believe that both the ability of the esterified cellulose ethers to form cross-links and their ability to form other chain interactions, such as chain association and/or chain aggregation, influence and, depending on the type of active ingredient like a drug, improve the solubility of the active ingredient like a drug in aqueous solutions and increases its bioavailability, i.e., its in vivo absorption by an individual upon ingestion. Without wanting to be bound by the theory, applicants also believe that esterified cellulose ethers that are not cross-linked but have a higher molecular weight than expected due to other chain interactions, such as hydrophobic/hydrophilic chain association and/or chain aggregation, have a decreased amount of undissolved particles in organic solvents, which is desirable for many end-use applications. E.g., a decreased amount of undissolved particles in organic solvents is desirable when an esterified cellulose ether is subjected to spray-drying to reduce or avoid clogging devices used for spray-drying, such as spray nozzles. Moreover, a decreased amount of undissolved particles in acetone solution is desirable when the esterified cellulose ethers are used in transparent films or coatings.

In the esterified cellulose ethers of the present invention the total weight fraction of the (non-methylated) esterified cellulose ether that exceeds 100,000 g/mol, Wf(>100 k), is caused by a larger extent by interactions of polymer chains that are reversible upon methylation of the —COOA groups and are caused to a smaller extent by cross-linked polymer chains, whose interaction is not reversible by methylation of the —COOA groups, than in known esterified cellulose ethers of comparable weight average molecular weight and comparable degrees of substitution. Accordingly, the term [Wf(>100 k)−Wf(>100 k)XL]/Wf(>100 k)XL is larger in the esterified cellulose ethers of the present invention than in known esterified cellulose ethers of comparable weight average molecular weight and comparable degrees of substitution. In the esterified cellulose ethers of the present invention [Wf(>100 k)−Wf(>100 k)XL]/Wf(>100 k)XL preferably is from 0.21 to 5.0, more preferably from 0.22 to 3.0, even more preferably from 0.23 to 1.2, most preferably from 0.24 to 0.60, and particularly from 0.24 to 0.50.

The esterified cellulose ethers of the present invention preferably have a viscosity of up to 5.0 mPa·s, more preferably up to 4.0 mPa·s, most preferably up to 3.6 mPa·s, and particularly up to 3.2 mPa·s, measured as a 2.0 wt % solution of the esterified cellulose ether in 0.43 wt % aqueous NaOH at 20° C. Generally the viscosity is at least 2.4 mPa·s, typically at least 2.5 mPa·s, measured as a 2.0 wt % solution of the esterified cellulose ether in 0.43 wt % aqueous NaOH at 20° C. The 2.0% by weight solution of the esterified cellulose ether is prepared as described in "Hypromellose Acetate Succinate, United States Pharmacopia and National Formulary, NF 29, pp. 1548-1550", followed by an Ubbelohde viscosity measurement according to DIN 51562-1: 1999-01 (January 1999). Esterified cellulose ethers of a low viscosity of up to 5.0 mPa·s, measured as a 2.0 wt % solution of the esterified cellulose ether in 0.43 wt % aqueous NaOH at 20° C., can be efficiently produced. It has been found that the viscosity of the esterified cellulose ether in 0.43 wt % aqueous NaOH substantially corresponds to the viscosity of the cellulose ether which is useful as a starting material for producing the esterified cellulose ether. A low viscosity cellulose ether used as a starting material allows for a good miscibility of the reaction mixture used for producing the esterified cellulose ethers of the present invention resulting in a homogeneous reaction mixture. Moreover, it has also been found that esterified cellulose ethers produced from low viscosity cellulose ethers exhibit a low viscosity in solution when subjected to high shear. This property is highly advantageous when an esterified cellulose ether is subjected to spray-drying, for example for preparing solid dispersions comprising an active ingredient and an esterified cellulose ether.

The esterified cellulose ethers of the present invention generally have a weight average molecular weight $M_w$ of from 80,000 to 350,000 Dalton, preferably from 90,000 to 300,000 Dalton, more preferably from 90,000 to 275,000 Dalton, most preferably from 100,000 to 250,000 Dalton, and particularly from 110,000 to 200,000 Dalton. The esterified cellulose ethers of the present invention generally have a number average molecular weight $M_n$ of from 23,000 to 150,000 Dalton, preferably from 25,000 to 80,000 Dalton, more preferably from 25,000 to 70,000 Dalton. The esterified cellulose ethers generally have a z-average molecular weight, $M_z$, of from 300,000 to 2,000,000 Dalton, more preferably from 500,000 to 1,8000,000 Dalton.

$M_w$, $M_n$ and $M_z$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0. The measurement of $M_w$, $M_n$ and $M_z$ is described in more details in the Examples.

The examples below describe how to prepare the esterified cellulose ethers of the present invention. Some aspects of the process for producing these esterified cellulose ethers will be described in more general terms below.

For producing an esterified cellulose ether of the present invention preferably a cellulose ether is used which has the type of ether groups and the degree(s) of substitution of ether groups as described further above. The cellulose ether preferably has a viscosity of from 2.4 to 5 mPa·s, more preferably from 2.5 to 4 mPa·s, and most preferably from 2.5 to 3.8 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The cellulose ether is reacted with (i) a dicarboxylic acid anhydride or (ii) a combination of an aliphatic monocarboxylic acid anhydride and a dicarboxylic acid anhydride. Preferred dicarboxylic acid anhydrides are selected from the group consisting of succinic anhydride, maleic anhydride and phthalic anhydride. Preferred aliphatic monocarboxylic acid anhydrides are selected from the group consisting of acetic anhydride, butyric anhydride and propionic anhydride. If a dicarboxylic acid anhydride and an aliphatic monocarboxylic acid anhydride are used in combination, the two anhydrides may be introduced into the reaction vessel at the same time or separately one after the other. The amount of each anhydride to be introduced into the reaction vessel is determined depending on the desired degree of esterification to be obtained in the final product, usually being 1 to 10 times the stoichiometric amounts of the desired molar degree of substitution of the anhydroglucose units by esterification. The molar ratio between the anhydride of a dicarboxylic acid and the anhydroglucose units of cellulose ether generally is 0.1/1 or more, and preferably 0.13 or more. The molar ratio between the anhydride of a dicarboxylic acid and the anhydroglucose units of cellulose ether generally is 1.5/1 or less, and preferably 1/1 or less. If an anhydride of a monocarboxylic acid is used, the molar ratio between the anhydride of an aliphatic monocarboxylic acid and the anhydroglucose units of the cellulose ether generally is 0.9/1 or more, and preferably 1.0/1 or more. The molar ratio between the anhydride of an aliphatic monocarboxylic acid and the anhydroglucose units of the cellulose ether generally is 8/1 or less, preferably 6/1 or less, and more preferably 4/1 or less. The molar number of anhydroglucose units of the cellulose ether utilized in the process of the present invention can be determined from the weight of the cellulose ether used as a starting material, by calculating the average molecular weight of the substituted anhydroglucose units from the DS(alkoxyl) and MS(hydroxyalkoxyl).

The esterification of the cellulose ether is preferably conducted in an aliphatic carboxylic acid as a reaction diluent, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid is preferably more than 50 percent, more preferably at least 75 percent, and even more preferably at least 90 percent, based on the total weight of the reaction diluent.

Most preferably the reaction diluent consists of an aliphatic carboxylic acid. The molar ratio [aliphatic carboxylic acid/anhydroglucose units of cellulose ether] is generally from [4.9/1.0] to [11.5/1.0], more preferably from [5.0/1.0] to [10.0/1.0], more preferably from [5.5/1.0] to [9.0/1.0], and most preferably from [5.8/1.0] to [9.0/1.0].

The esterification reaction is generally conducted in the presence of an esterification catalyst, preferably in the presence of an alkali metal carboxylate, such as sodium acetate or potassium acetate. The molar ratio [alkali metal carboxylate/anhydroglucose units of cellulose ether] is generally from [0.4/1.0] to [3.8/1.0], and preferably from [1.5/1.0] to [3.5/1.0].

Most preferably, the molar ratio [aliphatic carboxylic acid/anhydroglucose units of cellulose ether] is from [4.9/1.0] to [11.5/1.0], the molar ratio [alkali metal carboxylate/anhydroglucose units of cellulose ether] is from [0.4/1.0] to [3.3/1.0], the molar ratio [anhydride of aliphatic monocarboxylic acid/anhydroglucose units of cellulose ether] is from [0.9/1] to [3.0/1] and the molar ratio [anhydride of a dicarboxylic acid/anhydroglucose units of cellulose ether] is from [0.1/1] to [0.6/1].

Especially preferred, the molar ratio [anhydride of aliphatic monocarboxylic acid/anhydride of a dicarboxylic acid] is from [3.5/1] to [8.8/1] and the molar ratio [aliphatic carboxylic acid/anhydroglucose units of cellulose ether] is from [4.9/1.0] to [11.5/1.0].

The reaction mixture is generally heated at 60° C. to 110° C., preferably at 70 to 100° C., for a period of time sufficient to complete the reaction, that is, typically from 2 to 25 hours, more typically from 2 to 8 hours. The cellulose ether as the starting material is not always soluble in the aliphatic carboxylic acid, but can only be dispersed in or swollen by the aliphatic carboxylic acid, especially when the degree of substitution in the cellulose ether is relatively small. However, the reaction mixture should be thoroughly mixed to provide a homogeneous reaction mixture. As the esterification reaction proceeds, the cellulose ether under reaction generally dissolves in the reaction diluent.

After completion of the esterification reaction, the reaction product can be precipitated from the reaction mixture in a known manner, for example by contacting with a large volume of water, such as described in U.S. Pat. No. 4,226,981, International Patent Application WO 2005/115330 or European Patent Application EP 0 219 426. However, in a preferred embodiment of the invention the reaction product mixture is contacted with an amount of from 5 to 400, preferably from 8 to 300, more preferably from 10 to 100, and most preferably from 12 to 50 weight parts of water per weight part of cellulose ether used for esterification. The weight ratio [water/reaction product mixture excluding water] is generally from 1/1 to 10/1, preferably from 1.4/1 to 5/1, more preferably from 2/1 to 3/1. In a preferred embodiment of the invention the combination of water and the reaction product mixture is subjected to a shear rate of at least 800 $s^{-1}$, preferably at least 1500 $s^{-1}$, more preferably at least 3000 $s^{-1}$, and most preferably at least 8000 $s^{-1}$. The shear rate is generally up to 600,000 $s^{-1}$, and typically up to 500,000 $s^{-1}$. Applying such shear rates in the process of the present invention is useful for providing esters of cellulose ethers which are non-tacky and of fine particle size upon precipitation and separation from the reaction product mixture. According to known precipitation processes such non-tacky and fine particles are not achieved. This shear rate can be obtained in a high shear device, such as a high shear mixer, also known as rotor-stator mixer or homogenizer, high shear mill or high shear pump. A high shear device commonly comprises a rotor in combination with a stationary part of the shear device, also referred to as "stationary", such as a stator or housing. The stationary creates a close-clearance gap between the rotor and itself and forms a high-shear zone for materials in this gap. The stationary can include single or multiple rows of openings, gaps or teeth to induce a kind of shear frequency and increased turbulent energy. One metric for the degree or thoroughness of mixing is the shearing force generated by a mixing device with a high tip speed. Fluid undergoes shear when one area of fluid travels with a different velocity relative to an adjacent area. The tip speed of the rotor is a measure of the kinetic energy generated by the rotation according to the formula: Tip speed=rotation rate of rotor×rotor circumference. The shear rate is based on the inverse relationship between the gap distance between the rotor and the stationary part of the shear device which is commonly referred to as the stator or housing. In the case the high shear device is not equipped with a stator, the inner wall of a precipitation vessel serves as a stator. The formula applies: Shear rate=Tip speed/gap distance between outer diameter of rotor and stationary. The high shear device generally runs at a tip speed of at least 4 m/s, preferably at least 8 m/s, more preferably at least 15 m/s, and most preferably at least 30 m/s. The tip speed is generally up to 320 m/s, typically up to 280 m/s.

The dispersed esterified cellulose ether can subsequently be separated from the remainder of the mixture in a known manner, such as by centrifugation or filtration or upon settling by decantation. The recovered esterified cellulose ether can be washed with water to remove impurities and dried to produce an esterified cellulose ether in the form of a powder.

Another aspect of the present invention is a composition comprising a liquid diluent and one or more of the above described esterified cellulose ethers. The term "liquid diluent" as used herein means a diluent that is liquid at 25° C. and atmospheric pressure. The diluent can be water or an organic liquid diluent or a mixture of water and an organic liquid diluent. Preferably the amount of the liquid diluent is sufficient to provide sufficient fluidity and processability to the composition for the desired usage, such as spray-drying.

The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. Specific examples of preferred organic liquid diluents, optionally mixed with minor amounts of water are: methanol, tetrahydrofuran, methylene chloride, a blend of 80 to 95 weight percent of methanol and 20 to 5 weight percent of water, a blend of 80 to 95 weight percent of tetrahydrofuran and 20 to 5 weight percent of water, a blend of 55 to 85 weight percent of acetone and 45 to 15 weight percent of water, a blend of 15 to 85 weight percent of acetone and 85 to 15 weight percent of methanol, a blend of 15 to 85 weight percent of methyl ethyl ketone and 85 to 15 weight percent of methanol, a blend of 30 to 50 weight percent of acrylonitrile and 70 to 50 weight percent of a $C_{1-4}$-monoalcohol, such as methanol, ethanol, isopropylalcohol, or n-propanol; a blend of 30 to 50 weight percent of methanol and 70 to 50 weight percent of tetrahydrofuran or ethyl acetate, or a blend of 70 to 90 weight percent of ethanol and 10 to 30 weight percent of tetrahydrofuran or ethyl acetate.

In one embodiment the composition of the present invention comprises as liquid diluent an organic diluent alone or mixed with a minor amount of water. In this embodiment the composition of the present invention preferably comprises more than 50, more preferably at least 65, and most preferably at least 75 weight percent of an organic liquid diluent and preferably less than 50, more preferably up to 35, and most preferably up to 25 weight percent of water, based on the total weight of the organic liquid diluent and water. This embodiment of the invention is of particularly useful if the present invention comprises an active ingredient of poor water solubility.

In another embodiment the composition of the present invention comprises as liquid diluent water alone or mixed with a minor amount of an organic liquid diluent as described above. In this embodiment the composition of the present invention preferably comprises at least 50, more preferably at least 65, and most preferably at least 75 weight percent of water and preferably up to 50, more preferably up to 35, and most preferably up to 25 weight percent of an organic liquid diluent, based on the total weight of the organic liquid diluent and water. This embodiment of the invention is particularly useful for providing coatings or capsules from aqueous compositions comprising the esterified cellulose ether of the present invention. When preparing an aqueous solution, it is preferred that at least a portion of the groups of formula —C(O)—R—COOA are in their salt form.

The composition of the present invention comprising a liquid diluent and one or more of the above described esterified cellulose ethers is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers. The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The composition of the present invention preferably comprises from 1 to 40 weight percent, more preferably from 2.5 to 30 weight percent, most preferably from 5 to 25 weight percent, and particularly from 7 to 20 percent of at least one esterified cellulose ether as described above, from 40 to 99 weight percent, more preferably from 54.9 to 97.4 weight percent, most preferably from 65 to 94.5 weight percent and particularly from 70 to 92 percent of a liquid diluent described further above, and from 0 to 40 percent, preferably from 0.1 to 40 percent, most preferably from 0.5 to 25 percent, and particularly from 1 to 15 percent of an active ingredient, based on the total weight of the composition.

In one aspect of the invention the composition comprising at least one esterified cellulose ether as described above, one or more active ingredients and optionally one or more adjuvants can be used in liquid form, for example in the form of a suspension, a slurry, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with water as described above.

In another aspect of the invention the liquid composition of the present invention is used for producing a solid dispersion comprising at least one active ingredient, such as a drug described further above, at least one esterified cellulose ether as described above and optionally one or more adjuvants. The solid dispersion is produced by removing the liquid diluent from the composition.

One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25.

Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The above-mentioned components a), b) and optionally c) are preferably mixed in the form of particles, more preferably in powdered form. The components a), b) and optionally c) may be pre-mixed before feeding the blend into a device utilized for extrusion. Useful devices for extrusion, specifically useful extruders, are known in the art. Alternatively, the components a), b) and optionally c) may be fed separately into the extruder and blended in the device before or during a heating step. Preferably components a), b) and optionally c) are pre-blended in an extruder feeder and fed from there into the extruder. The composition or the component(s) that has or have been fed into an extruder are passed through a heated area of the extruder at a temperature which will melt or soften the composition or at least one or more components thereof to form a blend throughout which the active ingredient is dispersed. The blend is subjected to extrusion, preferably melt-extrusion, and caused to exit the extruder. Typical extrusion temperatures are from 50 to 210° C., preferably from 70 to 200° C., more preferably from 90 to 190° C., as determined by the setting for the extruder heating zone(s). An operating temperature range should be selected that will minimize the degradation or decomposition of the active ingredient and other components of the composition during processing. Single or multiple screw extruders, preferably twin screw extruders, can be used in the extrusion process. The molten or softened mixture obtained in the extruder is forced through one or more exit openings, such as one or more nozzles or dies. The molten or softened mixture then exits via a die or other such element having one or a plurality of openings, at which time, the extruded blend (now called the extrudate) begins to harden. Since the extrudate is still in a softened state upon exiting the die, the extrudate may be easily shaped, molded, chopped, spheronized into beads, cut into strands, tabletted or otherwise processed to the desired physical form. The extrudate can optionally be cooled to hardening and ground into a powdered form.

The solid dispersion of the present invention preferably comprises from 20 to 99.9 percent, more preferably from 30 to 98 percent, and most preferably from 60 to 95 percent of an esterified cellulose ether a) as described above, and preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, are one or more of the adjuvants c) as described below. The solid dispersion can comprise one or more of the esterified cellulose ethers a), one or more of the active ingredients b), and optionally one or more of the adjuvants c), however their total amount is generally within the above-mentioned ranges.

Once the solid dispersion comprising at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms. The solid dispersion of the present invention may be in various forms, such as, e.g. in the form of strands, pellets, granules, pills, tablets, caplets, microparticles, fillings of capsules or injection molded capsules or in the form of a powder, film, paste, cream, suspension or slurry.

The amount of the active ingredient in the dosage form is generally is at least 0.1 percent, preferably at least 1 percent, more preferably at least 3 percent, most preferably at least 5 percent and generally up to 70 percent, preferably up to 50 percent, more preferably up to 30 percent, most preferably up to 25 percent, based on the total weight of the dosage form.

In another aspect of the invention the composition of the present invention comprising a liquid diluent and one or more of the above described esterified cellulose ethers may be used for coating dosage forms, such as tablets, granules, pellets, caplets, lozenges, suppositories, pessaries or implantable dosage forms, to form a coated composition. If the composition of the present invention comprises an active ingredient, such as a drug, drug layering can be achieved, i.e., the dosage form and the coating may comprise different active ingredients for different end-uses and/or having different release kinetics.

In yet another aspect of the invention the composition of the present invention comprising a liquid diluent and one or more of the above described esterified cellulose ethers may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants, and any combination thereof. Optional additives are preferably pharmaceutically acceptable. Useful amounts and types of one or more optional adjuvants are generally known in the art and depend on the intended end-use of the liquid composition or the solid dispersion of the present invention.

The following examples are for illustrative purposes only and are not intended to limit the scope of the present invention.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The ester substitution with acetyl groups (—CO—$CH_3$) and the ester substitution with succinoyl groups (—CO—$CH_2$—$CH_2$—COOH) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Determination of Wf(>100 k) and Wf(>100 k)XL

Reagents and Chemicals:
1) HPLC grade tetrahydrofuran (THF), unstabilized.
2) Reagent grade N, N-dimethylformamide (DMF)
3) Dimethylformamide-dimethylacetal (DMF-DMA) in 1 gram sealed glass ampoules
4) Narrow polystyrene (PS) molecular weight standards from Agilent, Incorporated covering the molecular weight range from 3,742 to 0.58 kg/mol.

THF Size-Exclusion-Chromatography (SEC) System:

Apparent molecular weight distributions (MWDs) of HPMCAS and methylated HPMCAS were determined by SEC. The SEC system was based on a Waters Alliance 2695 operated at 1 mL/minute. The eluent was HPLC grade THF that was continuously degassed with the online vacuum degasser within the Alliance 2695. The Waters Alliance 2695 was programmed to inject 200 microliters of sample solutions. Duplicate injections were made for each sample solution. SEC separations were performed on a series of three, 7.5 mm i d×300 mm length TSKgel GMH$_{HR}$-H 30 µm mixed bed columns from TOSOH Bioscience. The differential refractive index detector within a Viscotek Model 302 triple detector array was used for detection. Columns and detectors were operated at 35° C. SEC chromatograms were collected and reduced via OmniSEC software version 4.0 from Viscotek. 17 narrow PS molecular weight standards (Agilent, Inc.) covering the molecular weight range from 0.58 to 3742 kg/mol were used for column calibration. The standards were prepared as cocktails at concentrations of 0.5 mg/ml each in THF. The calibration curve was least squares fit to a first order polynomial. Molecular weight distributions were calculated from the DRI detector chromatogram and the PS calibration curve under the assumption of constant refractive index increment across the SEC chromatogram. All references to molecular weight are not absolute, but linear PS equivalent values.

Methylation of HPMCAS:

A 0.03 g aliquot (accurately weighed to the nearest 0.0001 g) of HPMCAS was weighed into a 15 mL headspace gas chromatography vial. One mL of DMF solvent and the contents of 1 ampoule (~0.94 g) of dimethylformamide-dimethylacetal DMF-DMA were added to the HPMCAS sample in the headspace gas chromatography vial. The vials were crimped with Teflon coated caps, and placed on a heated block shaker set at ~78° C. and were shaken for 90 minutes. After cooling to ambient temperature, the vial caps were removed, and the solutions were placed under a gentle stream of $N_2$ at ambient temperature overnight to completely evaporate the DMF and excess DMF-DMA. The residue was reconstituted in 10 mL of THF resulting in a final solution concentration of 3 mg/mL. The solution was re-capped and was shaken at ambient temperature until dissolved (at least 45 minutes). The solutions were filtered through a 0.45 µm PTFE filter, and injected onto the THF SEC system.

HPMCAS for SEC Analysis:

Unmethylated HPMC-AS was prepared for SEC analysis by accurately weighing a 0.03 g aliquot to the nearest 0.0001 g into a laboratory vial. A 10 ml aliquot of THF was added and the sample solution was shaken at ambient temperature on a flat bed shaker for ~2 hours to dissolve resulting in a final HPMC-AS concentration of 3 mg/mL. The solutions were filtered through a 0.45 µm PTFE filter, and injected onto the SEC system.

Determination of [Wf(>100 k)−Wf(>100 k)XL]/Wf(>100 k)XL:

A) The SEC chromatogram of HPMCAS in THF contains contributions from i) linear polymer chains, ii) cross-linked polymer chains and iii) associated and/or aggregated polymer chains. Wf(>100 k) designates the total weight fraction of the HPMCAS that exceeds 100,000 g/mol.

B) Conversion of the acid groups from succinate substitution to their methyl esters successfully eliminated chain association and aggregation in THF. Thus, the SEC chromatogram of methylated HPMCAS in THF includes contributions from i) linear polymer chains, and ii) cross-linked polymer chains, only. Wf(>100 k)XL designates the weight fraction that exceeds 100,000 g/mol of the methylated HPMCAS.

C) Calculating the difference [Wf(>100 k)−Wf(>100 k)XL] enables the determination of contributions of associated and/or aggregated polymer chains in the weight fraction of the molecular weight distribution that exceeds 100,000 g/mol.

D) Since the weight average molecular weight $M_w$ of the HPMC used in the Examples (Methocel E3 LV Premium cellulose ether) is only about 20,000 g/mol, at hydrodynamic size larger than 100 kg/mol PS-equivalent, essentially no contributions from i) linear chains are expected in the SEC chromatogram of HPMCAS or methylated HPMCAS due to the lack of chains in this size regime in the starting MWD of the HMPC feedstock material. Thus, contributions to the MWD in HPMCAS exceeding 100 kg/mol PS-equivalent come from the sum of ii) cross-linked polymer chains and iii) associated and/or aggregated polymer chains. In methylated HPMCAS, the weight fraction exceeding 100 kg/mol essentially comprises cross-linked polymer chains, only. The calculation of [Wf(>100 k)−Wf(>100 k)XL]/Wf(>100 k)XL allows a differentiation between the contributions from chain association and/or aggregation and the contributions from chain cross-linking in this high molecular weight fraction of the molecular weight distribution in the esterified cellulose ethers of the present invention and of the prior art, such as the HPMCAS of the Examples and the Comparative Examples.

Determination of $M_w$, $M_n$ and $M_z$

Mw, Mn and Mz are measured according to Journal of Pharmaceutical and Biomedical Analysis 56 (2011) 743 unless stated otherwise. The mobile phase was a mixture of 40 parts by volume of acetonitrile and 60 parts by volume of aqueous buffer containing 50 mM NaH2PO4 and 0.1 M NaNO3. The mobile phase was adjusted to a pH of 8.0. Solutions of the cellulose ether esters were filtered into a HPLC vial through a syringe filter of 0.45 µm pore size.

More specifically, the utilized Chemicals and solvents were:

Polyethylene oxide standard materials (abbreviated as PEOX 20 K and PEOX 30 K) were purchased from Agilent Technologies, Inc. Palo Alto, Calif., catalog number PL2083-1005 and PL2083-2005.

Acetonitrile (HPLC grade ≥99.9%, CHROMASOL plus), catalog number 34998, sodium hydroxide (semiconductor grade, 99.99%, trace metal base), catalog number 306576, water (HPLC grade, CHROMASOLV Plus) catalog number 34877 and sodium nitrate (99,995%, trace metal base) catalog number 229938 were purchased from Sigma-Aldrich, Switzerland.

Sodium dihydrogen phosphate (≥99.999% TraceSelect) catalog number 71492. was purchased from FLUKA, Switzerland.

The normalization solution of PEOX20 K at 5 mg/mL, the standard solution of PEOX30 K at 2 mg/mL, and the sample solution of HPMCAS at 2 mg/mL were prepared by adding a weighed amount of polymer into a vial and dissolving it with a measured volume of mobile phase. All solutions were allowed to dissolve at room temperature in the capped vial for 24 h with stirring using a PTFE-coated magnetic stirring bar.

The normalization solution (PEOX 20 k, single preparation, N) and the standard solution (PEOX30 K, double preparation, S1 and S2) were filtered into a HPLC vial through a syringe filter of 0.02 µm pore size and 25 mm diameter (Whatman Anatop 25, catalog number 6809-2002), Whatman.

The test sample solution (HPMCAS, prepared in duplicate, T1, T2) and a laboratory standard (HPMCAS, single preparation, LS) were filtered into a HPLC vial through a syringe filter of 0.45 µm pore size (Nylon, e.g. Acrodisc 13 mm VWR catalog number 514-4010).

Chromatographic condition and run sequence were conducted as described by Chen, R. et al.; Journal of Pharmaceutical and Biomedical Analysis 56 (2011) 743-748). The SEC-MALLS instrument set-up included a HP1100 HPLC system from Agilent Technologies, Inc. Palo Alto, Calif.; a DAWN Heleos II 18 angle laser light scattering detector and a OPTILAB rex refractive index detector, both from Wyatt Technologies, Inc. Santa Barbara, Calif. The analytical size exclusion column (TSK-GEL® GMPWXL, 300×7.8 mm) was purchased from Tosoh Bioscience. Both the OPTILAB and the DAWN were operated at 35° C. The analytical SEC column was operated at room temperature (24±5° C.). The mobile phase was a mixture of 40 volume parts of acetonitrile and 60 volume parts of aqueous buffer containing 50 mM NaH2PO4 and 0.1 M NaNO3 prepared as follows:

Aqueous buffer: 7.20 g of sodium dihydrogen phosphate and 10.2 g of sodium nitrate were added to 1.2 L purified water in a clean 2 L glass bottle under stirring until dissolution.

Mobile phase: 800 mL of acetonitrile were added to 1.2 L of the aqueous buffer prepared above, and stirred until a good mixture was achieved and the temperature equilibrated to ambient temperature.

The mobile phase was pH adjusted to 8.0 with 10M NaOH and filtered through a 0.2 m nylon membrane filter. The flow rate was 0.5 mL/min with in-line degassing. The injection volume was 100 µL and the analysis time was 35 min The MALLS data were collected and processed by Wyatt ASTRA software (version 5.3.4.20) using do/dc value (refractive index increment) of 0.120 mL/g for HPMCAS. The light scattering signals of detector Nos. 1-4, 17, and 18) were not used in the molecular weight calculation. A representative chromatographic run sequence is given below: B, N, LS, S1 (5×), S2, T1 (2×), T2 (2×), T3 (2×), T4 (2×), S2, T5(2×), etc., S2, LS, W, where, B represents blank injection of mobile phase, N1 represents normalization solution; LS represents a laboratory standard HPMCAS; S1 and S2 represent standard solutions one and two, respectively; T1, T2, T3, T4, and T5 represent test sample solutions and W represents water injection. (2×) and (5×) denote the number of injections of the same solution.

Both the OPTILAB and the DAWN were calibrated periodically according to the manufacturer's recommended procedures and frequency. A 100 µL injection of a 5 mg/mL polyethylene oxide standard (PEOX20 K) was employed for normalizing all angle light scattering detectors relative to 90° detector for each run sequence.

Use of this mono-dispersed polymer standard also enabled the volume delay between the OPTILAB and the DAWN to be determined, permitting proper alignment of the light scattering signals to the refractive index signal. This is necessary for the calculation of the weight-averaged molecular weight (Mw) for each data slice.

Production of Hydroxypropyl Methyl Cellulose Acetate Succinate (HPMCAS) of Examples 1-8

Glacial acetic acid, acetic anhydride, a hydroxypropyl methylcellulose (HPMC), succinic anhydride and sodium acetate (water free) were introduced in the amounts listed in Table 1 below into a reaction vessel under thorough stirring.

The HPMC had a methoxyl and hydroxypropyl substitution as listed in Tables 2 and 3 below and a viscosity of about 3 mPa·s, measured as a 2% solution in water at 20° C. according to ASTM D2363-79 (Reapproved 2006). The HPMC is commercially available from The Dow Chemical Company as Methocel E3 LV Premium cellulose ether.

The mixture was heated at 85° C. with agitation for 3 or 3.5 hours, as listed in Table 1 below, to effect esterification. x L of water was added to the reactor under stirring to precipitate the HPMCAS. The precipitated product was removed from the reactor and washed with y L of water by applying high shear mixing using an Ultra-Turrax stirrer S50-G45 running at 5200 rpm. The numbers of water x and y are listed in Table 1 below. The product was isolated by filtration and dried at 50° C. overnight.

Production of HPMCAS of Comparative Examples A and B

The production of HPMCAS according to Comparative Examples A and B was carried out as in Examples 1 to 8, except that the weight ratios of glacial acetic acid, acetic anhydride, HPMC, succinic anhydride and sodium acetate were used as disclosed in Example 2 of European Patent Application EP 0219 426 A2, as listed in Table 1 below.

The HPMC used in Comparative Examples A and B respectively had a viscosity of about 6 mPa·s and about 3 mPa·s respectively, measured as a 2% solution in water at 20° C. according to ASTM D2363-79 (Reapproved 2006). Each HPMC contained about 10% by weight of hydroxypropoxyl groups and about 29% by weight of methoxyl groups. These HPMC's are commercially available from The Dow Chemical Company as Methocel E6 LV Premium cellulose ether and Methocel E3 LV Premium cellulose ether respectively.

The mixture was heated at 85° C. with agitation for 3.5 hours to effect esterification. x L of water was added to the reactor under stirring to precipitate the HPMCAS. The precipitated product was removed from the reactor and washed with y L of water by applying high shear mixing using an Ultra-Turrax stirrer S50-G45 running at 5200 rpm. The numbers of water x and y are listed in Table 1 below. The product was isolated by filtration and dried at 55° C. for 12 h.

Production of Comparative Example C

The production of HPMCAS according to Comparative Example C was carried out as in Examples 1 to 8, except that the weight ratios of glacial acetic acid, acetic anhydride, HPMC, succinic anhydride and sodium acetate were used as disclosed in Comparative Example 3 of U.S. Pat. No. 5,776,501 and as listed in Table 1 below. The HPMC used in Comparative Example 3 of U.S. Pat. No. 5,776,501 had a viscosity of 8.9 mPa·s, measured as a 2% solution in water. However, to avoid that differences in HPMC viscosity have an impact on the molecular weight of the HPMCAS, the same HPMC was used in Comparative Example C as in Examples 1-8.

The mixture was heated at 85° C. with agitation for 5 hours to effect esterification. 252.86 g of water was added to the reactor under stirring, followed by addition of 70.71 g concentrated hydrochloric acid (concentration of 37 wt-%). The precipitated product was obtained by adding the reaction mixture to 3.0 L of water under stirring (200 rpm). The crude product was washed with 11 L of water by applying high shear mixing using an Ultra-Turrax stirrer S50-G45 running at 5200 rpm. The product was isolated by filtration and dried at 55° C. for 12 h.

Repetition of Comparative Examples A-C

The obtained ester substitutions % acetyl and % succinoyl in Comparative Examples A and B were significantly different from those disclosed in Example 2 of European Patent Application EP 0219 426 A2. In Comparative Example C the obtained ester substitutions % acetyl and % succinoyl matched reasonably well with the ester substitutions reported in Comparative Example 3 of U.S. Pat. No. 5,776, 501.

Therefore, Comparative Examples A-C were repeated. The obtained ester substitutions % acetyl and % succinoyl in the repeated set of Comparative Examples A-C were substantially the same as in the first set of Comparative Examples A-C. The obtained ester substitutions % acetyl and % succinoyl in Tables 2 and 3 show the average of the two sets of Comparative Examples A, B, and C.

Production of Comparative Examples D-H

The production of HPMCAS according to Comparative Examples D-H was carried out as in Examples 1 to 8, except that the weight ratios of glacial acetic acid, acetic anhydride, HPMC, succinic anhydride and sodium acetate were used as disclosed in Example 1 of U.S. Pat. No. 4,226,981, Table I, Sample Nos. 1-5. The used amounts are listed in Table 1 below. The U.S. Pat. No. 4,226,981 is silent about the viscosity of the used HPMC. To avoid that differences in HPMC viscosity have an impact on the molecular weight of the HPMCAS, the same HPMC was used in Comparative Example D-H as in Examples 1-8. x L of water was added to the reactor under stirring to precipitate the HPMCAS. The precipitated product was removed from the reactor and washed with y L of water by applying high shear mixing using an Ultra-Turrax stirrer S50-G45 running at 5200 rpm. The numbers of water x and y are listed in Table 1 below.

Production of Comparative Examples I and J

The production of HPMCAS according to Comparative Example I and J was carried out as in Examples 1 to 8, except that the weight ratios of glacial acetic acid, acetic anhydride, HPMC, succinic anhydride and sodium acetate were used as disclosed International Patent Application WO 2005/115330, pages 51 and 52, polymers 1 and 3. The product was obtained, separated and washed as described in International Patent Application WO 2005/115330. The reaction mixture was quenched into 2.4 L of water, precipitating the polymer. An additional 1 L of water was used to complete the precipitation for example I only. The polymer was then isolated and washed with 3×300 mL of water. Then the polymer was dissolved in 600 mL of acetone and again precipitated in 2.4 L of water. To complete precipitation another 1 L of water was added.

Comparative Examples K to M

As disclosed in International Patent Application WO 2011/159626 on pages 1 and 2, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed below. Samples of the commercially available materials were analyzed as described further above.

Properties of AQOAT polymers as listed in WO 2011/159626:

| | Designation of analyzed commercial samples: Comparative Example | | |
|---|---|---|---|
| | K | L | M |
| | Published Composition of AQOAT polymers (wt %) | | |
| Substituent content | L-Grade | M-Grade | H-Grade |
| Methoxyl | 20.0-24.0 | 21-0-25.0 | 22.0-26.0 |
| Hydroxypropoxyl | 5.0-9.0 | 5.0-9.0 | 6.0-10.0 |
| Acetyl | 5.0-9.0 | 7.0-11.0 | 10.0-14.0 |
| Succinoyl | 14.0-18.0 | 10-14 | 4.0-8.0 |

Comparative Example N: Hydroxypropyl Methyl Cellulose Phthalate (HPMCP)

HPMCP was produced from Methocel E3 LV Premium cellulose ether as described in Example 1 of European Patent Application EP 0219 426 A2. The produced HPMCP had a [Wf(>100 k)−Wf(>100 k)XL]/Wf(>100 k)XL of 0.00.

Comparative Example O: Hydroxypropyl Methyl Cellulose Phthalate (HPMCP)

HPMCP was produced from Methocel E3 LV Premium cellulose ether as described on pages 38 and 39 of the International Patent Application WO 2006/082518. The produced HPMCP had a Wf(>100 k) of 12.7%, a Wf(>100 k)XL of 11.9%, and a [Wf(>100 k)−Wf(>100 k)XL]/Wf(>100 k)XL of 0.07.

Comparative Examples P, Q-1, Q-2, R-1 and R-2

HPMCAS samples were produced as described on pages 34 and 35 of WO 2011/159626. In Comparative Example P the recipe for HPMCAS-K(1) was exactly repeated. In Comparative Examples Q-1 and Q-2 the recipe for HPMCAS-K(2) and in Comparative Examples R-1 and R-2 the recipe for HPMCAS-K(3) were exactly repeated. Comparative Examples Q and R were each conducted twice and reported as Q-1, Q-2, R-1 and R-2 respectively since the results in Comparative Examples Q-1 and R-1 for $DOS_{Ac}$ and $DOS_S$ deviated from the results reported in WO 2011/159626 for HPMCAS-K(2) and HPMCAS-K(3).

The properties of the HPMCAS produced according to Examples 1-8 and comparative Examples A-J, N, O, P, Q-1, Q-2, R-1 and R-2 and the properties of the commercially available Comparative Examples K to M are listed in Tables 2 and 3 below.

In Tables 2 and 3 below the abbreviations have the following meanings:

$DS_M$=DS(methoxyl): degree of substitution with methoxyl groups;

$MS_{HP}$=MS(hydroxypropoxyl): molar subst. with hydroxypropoxyl groups;

$DOS_{Ac}$: degree of substitution of acetyl groups;

$DOS_S$: degree of substitution of succinoyl groups.

TABLE 1

| (Comp.) Example | HPMC* g | HPMC* Mol | acetic acid g | acetic acid mol/mol HPMC | Succinic anhydride g | Succinic anhydride mol/mol HPMC | Acetic anhydride g | Acetic anhydride mol/mol HPMC | Sodium acetate g | Sodium acetate mol/mol HPMC | Heating at 85° C. hours | x L of water | y L of water |
|---|---|---|---|---|---|---|---|---|---|---|---|---|---|
| 1 | 150 | 0.74 | 500 | 11.2 | 42.0 | 0.57 | 195.0 | 2.69 | 150.0 | 2.47 | 3.5 | 1.8 | 32 |
| 2 | 187.5 | 0.93 | 500 | 9.0 | 52.5 | 0.57 | 243.8 | 2.69 | 187.5 | 2.47 | 3.5 | 1.8 | 35 |
| 3 | 195 | 0.97 | 440 | 7.6 | 45.0 | 0.47 | 210.0 | 2.27 | 170.0 | 2.15 | 3 | 1.8 | 24 |
| 4 | 195 | 0.97 | 440 | 7.6 | 40.0 | 0.42 | 200.0 | 2.12 | 195.0 | 2.47 | 3 | 1.8 | 16 |
| 5 | 230 | 1.14 | 521 | 7.6 | 64.4 | 0.57 | 299.0 | 2.69 | 259.5 | 2.78 | 3 | 2.1 | 20 |
| 6 | 230 | 1.14 | 521 | 7.6 | 64.4 | 0.57 | 299.0 | 2.69 | 283.1 | 3.04 | 3 | 2.1 | 20 |
| 7 | 230 | 1.14 | 335 | 4.9 | 17.4 | 0.15 | 126.5 | 1.14 | 49.3 | 0.53 | 3.5 | 2.3 | 15 |
| 8 | 230 | 1.14 | 350 | 5.1 | 38.8 | 0.34 | 142.6 | 1.28 | 50 | 0.54 | 3.5 | 2.3 | 14 |
| A[1] | 100 | 0.49 | 300 | 10.1 | 25 | 0.51 | 38 | 0.78 | 80 | 1.97 | 3.5 | 1.2 | 12 |
| B[2] | 200 | 0.96 | 600 | 10.2 | 50 | 0.51 | 76 | 0.78 | 160 | 1.97 | 3.5 | 2.4 | 11 |
| C | 150 | 0.74 | 450 | 10.1 | 35.8 | 0.48 | 57.43 | 0.79 | 59.57 | 0.98 | 5 | 3.0 | 11 |
| D | 115 | 0.57 | 575 | 16.9 | 138 | 2.44 | 57.5 | 1.03 | 115 | 2.47 | 3 | 2.3 | 10 |
| E | 115 | 0.57 | 575 | 16.9 | 92 | 1.63 | 57.5 | 1.03 | 115 | 2.47 | 3 | 2.3 | 10 |
| F | 115 | 0.57 | 575 | 16.9 | 57.5 | 1.02 | 115 | 2.06 | 115 | 2.47 | 3 | 2.3 | 10 |
| G | 115 | 0.57 | 575 | 16.9 | 46 | 0.81 | 138 | 2.48 | 115 | 2.47 | 3 | 2.3 | 10 |
| H | 115 | 0.57 | 575 | 16.9 | 34.5 | 0.61 | 184 | 3.30 | 115 | 2.47 | 3 | 2.3 | 10 |
| I | 80 | 0.40 | 420 | 17.7 | 18.9 | 0.48 | 640.2 | 16.53 | 40.43 | 1.25 | 21.75 | See Comp. Examples | |
| J | 80 | 0.40 | 420 | 17.7 | 13.2 | 0.33 | 432.8 | 11.17 | 40.43 | 1.25 | 21.75 | I and J above | |

*calculated on the dried basis
[1] Comparative Example A: HPMC of 6 mPa·s
[2] Comparative Example B: HPMC of 3 mPa·s

TABLE 2

| | Ether Substitution | | | | | Ester substitution | | Ether Substitution | | Ester substitution | |
|---|---|---|---|---|---|---|---|---|---|---|---|
| (Comp.) Example | Wf(>100k) (%) | Wf(>100k)XL (%) | [Wf(>100k) − Wf(>100k)XL]/ Wf(>100k)XL | Methoxyl, % | Hydroxy-propoxyl, % | Acetyl (%) | Succinoyl, % | $DS_M$ | $MS_{HP}$ | $DOS_{Ac}$ | $DOS_s$ |
| 1 | 25.6 | 20.0 | 0.28 | 22.8 | 7.5 | 10.4 | 12.4 | 1.94 | 0.26 | 0.64 | 0.32 |
| 2 | 29.9 | 22.6 | 0.32 | 22.8 | 7.5 | 10.6 | 12.4 | 1.94 | 0.26 | 0.65 | 0.32 |
| 3 | 31.6 | 23.6 | 0.34 | 23.1 | 7.5 | 10.1 | 13.2 | 1.98 | 0.27 | 0.63 | 0.35 |
| 4 | 33.1 | 25.8 | 0.28 | 22.9 | 7.5 | 9.9 | 12.3 | 1.93 | 0.26 | 0.60 | 0.32 |
| 5 | 33.7 | 27.2 | 0.24 | 22.7 | 7.2 | 10.7 | 12.3 | 1.93 | 0.25 | 0.65 | 0.32 |
| 6 | 34.4 | 27.1 | 0.27 | 22.6 | 7.2 | 10.9 | 12.4 | 1.93 | 0.25 | 0.67 | 0.32 |
| 7 | 31.9 | 21.4 | 0.49 | 24.1 | 7.8 | 11.5 | 5.6 | 1.90 | 0.25 | 0.65 | 0.14 |
| 8 | 32.9 | 26.3 | 0.25 | 23.3 | 7.5 | 8.9 | 10.6 | 1.89 | 0.25 | 0.52 | 0.26 |
| A[1] | 35.9 | 34.2 | 0.05 | 21.9 | 7.2 | 5.6 | 16.8 | 1.83 | 0.25 | 0.34 | 0.43 |
| B[2] | 23.8 | 20.2 | 0.18 | 22.9 | 7.3 | 5.7 | 16.0 | 1.91 | 0.25 | 0.34 | 0.41 |

TABLE 2-continued

| | | | Ether Substitution | | | Ester substitution | | Ether Substitution | | Ester substitution | |
|---|---|---|---|---|---|---|---|---|---|---|---|
| (Comp.) Example | Wf(>100k) (%) | [Wf(>100k)] Wf(>100k)XL (%) | [Wf(>100k)−Wf(>100k)XL]/ Wf(>100k)XL | Methoxyl, % | Hydroxy-propoxyl, % | Acetyl (%) | Succinoyl, % | $DS_M$ | $MS_{HP}$ | $DOS_{Ac}$ | $DOS_S$ |
| C | 15.9 | 15.9 | 0.00 | 23.7 | 7.6 | 5.8 | 14.7 | 1.96 | 0.26 | 0.35 | 0.37 |
| D | 12.0[3] | 19.7 | [3] | 20.10 | 6.40 | 2.60 | 25.00 | 1.79 | 0.24 | 0.17 | 0.68 |
| E | 12.5[3] | 18.5 | [3] | 21.60 | 6.60 | 3.30 | 22.70 | 1.90 | 0.24 | 0.21 | 0.61 |
| F | 18.1 | 18.1 | 0.00 | 21.60 | 7.00 | 6.20 | 15.80 | 1.79 | 0.24 | 0.37 | 0.40 |
| G | 19.6 | 17.9 | 0.10 | 23.10 | 7.20 | 7.80 | 13.50 | 1.92 | 0.25 | 0.47 | 0.34 |
| H | 19.1 | 16.2 | 0.18 | 23.50 | 7.60 | 9.68 | 9.63 | 1.90 | 0.25 | 0.57 | 0.24 |
| I | 20.0 | 18.9 | 0.06 | 22.3 | 7.40 | 11.70 | 11.70 | 1.90 | 0.26 | 0.72 | 0.31 |
| J | 21.6 | 18.3 | 0.18 | 22.6 | 7.1 | 12.6 | 9.1 | 1.88 | 0.24 | 0.75 | 0.23 |
| K | 34.7 | 31.0 | 0.12 | 22.50 | 7.00 | 8.10 | 14.70 | 1.90 | 0.24 | 0.49 | 0.38 |
| L | 30.3 | 27.2 | 0.12 | 23.10 | 7.30 | 9.30 | 10.60 | 1.88 | 0.24 | 0.54 | 0.26 |
| M | 32.5 | 29.2 | 0.11 | 23.60 | 7.20 | 11.50 | 7.80 | 1.90 | 0.24 | 0.67 | 0.19 |
| P | | recovery rate only 76% | | 15.7 | 6.2 | 12.1 | 20.8 | 1.47 | 0.24 | 0.82 | 0.60 |
| Q-1 | | recovery rate only 62% | | 16.2 | 6.3 | 14.3 | 16.6 | 1.47 | 0.24 | 0.94 | 0.46 |
| Q-2 | | recovery rate only 58% | | 15.8 | 6.0 | 14.8 | 17.1 | 1.45 | 0.23 | 0.98 | 0.48 |
| R-1 | | recovery rate only 82% | | 17.2 | 6.6 | 19.1 | 8.2 | 1.49 | 0.24 | 1.19 | 0.22 |
| R-2 | | recovery rate only 85% | | 16.9 | 6.4 | 19.0 | 8.7 | 1.47 | 0.23 | 1.19 | 0.23 |

[1] Comparative Example A: HPMC of 6 mPa·s
[2] Comparative Example B: HPMC of 3 mPa·s
[3] No reliable measurement possible due to low recovery

TABLE 3

| | | | | 2% | Ether Substitution | | Ester substitution | | Ether Substitution | | Ester substitution | |
|---|---|---|---|---|---|---|---|---|---|---|---|---|
| (Comp.) Example | Mw | Mol. weight (kDA) Mn | Mz | viscosity* (mPa·s) | Methoxyl (%) | Hydroxy-Propoxyl, (%) | Acetyl (%) | Succinoyl (%) | $DS_M$ | $MS_{HP}$ | $DOS_{Ac}$ | $DOS_S$ |
| 1 | 68 | 22 | 722 | 2.63 | 22.8 | 7.5 | 10.4 | 12.4 | 1.94 | 0.26 | 0.64 | 0.32 |
| 2 | 113 | 31 | 1320 | 2.61 | 22.8 | 7.5 | 10.6 | 12.4 | 1.94 | 0.26 | 0.65 | 0.32 |
| 3 | 142 | 38 | 912 | 2.61 | 23.1 | 7.5 | 10.1 | 13.2 | 1.98 | 0.27 | 0.63 | 0.35 |
| 4 | 144 | 38 | 907 | 2.64 | 22.9 | 7.5 | 9.9 | 12.3 | 1.93 | 0.26 | 0.60 | 0.32 |
| 5 | 195 | 57 | 1073 | 2.65 | 22.7 | 7.2 | 10.7 | 12.3 | 1.93 | 0.25 | 0.65 | 0.32 |
| 6 | 248 | 75 | 1235 | 2.70 | 22.6 | 7.2 | 10.9 | 12.4 | 1.93 | 0.25 | 0.67 | 0.32 |
| 7 | 142 | 44 | 1018 | 2.97 | 24.1 | 7.8 | 11.5 | 5.6 | 1.90 | 0.25 | 0.65 | 0.14 |
| 8 | 226 | 75 | 1037 | 2.93 | 23.3 | 7.5 | 8.9 | 10.6 | 1.89 | 0.25 | 0.52 | 0.26 |
| A[1] | 270 | 87 | 1060 | 4.58 | 21.9 | 7.2 | 5.6 | 16.8 | 1.83 | 0.25 | 0.34 | 0.43 |
| B[2] | 65 | 26 | 329 | 2.89 | 22.9 | 7.3 | 5.7 | 16.0 | 1.97 | 0.25 | 0.34 | 0.41 |
| C | 53 | 23 | 342 | 2.90 | 23.7 | 7.6 | 5.8 | 14.7 | 1.96 | 0.26 | 0.35 | 0.37 |
| D | 37 | 25 | 56 | 3.06 | 20.10 | 6.40 | 2.60 | 25.00 | 1.79 | 0.24 | 0.17 | 0.68 |
| E | 38 | 25 | 65 | 2.89 | 21.60 | 6.60 | 3.30 | 22.70 | 1.90 | 0.24 | 0.21 | 0.61 |
| F | 41 | 23 | 111 | 2.92 | 21.60 | 7.00 | 6.20 | 15.80 | 1.79 | 0.24 | 0.37 | 0.40 |
| G | 40 | 22 | 123 | 2.98 | 23.10 | 7.20 | 7.80 | 13.50 | 1.92 | 0.25 | 0.47 | 0.34 |
| H | 36 | 20 | 119 | 3.73 | 23.50 | 7.60 | 9.68 | 9.63 | 1.90 | 0.25 | 0.57 | 0.24 |
| I | 51 | 23 | 462 | 2.86 | 22.3 | 7.40 | 11.70 | 11.70 | 1.90 | 0.26 | 0.72 | 0.31 |
| J | 54 | 22 | 1158 | 2.86 | 22.6 | 7.1 | 12.6 | 9.1 | 1.88 | 0.24 | 0.75 | 0.23 |
| K | 151 | 31 | 822 | 3.00 | 22.50 | 7.00 | 8.10 | 14.70 | 1.90 | 0.24 | 0.49 | 0.38 |
| L | 114 | 27 | 654 | 2.94 | 23.10 | 7.30 | 9.30 | 10.60 | 1.88 | 0.24 | 0.54 | 0.26 |
| M | 142 | 28 | 835 | 2.89 | 23.60 | 7.20 | 11.50 | 7.80 | 1.90 | 0.24 | 0.67 | 0.19 |
| P | 427 | 94 | 2592 | 2.06 | 15.7 | 6.2 | 12.1 | 20.8 | 1.47 | 0.24 | 0.82 | 0.60 |
| Q-1 | recovery rate only 71% | | | 2.05 | 16.2 | 6.3 | 14.3 | 16.6 | 1.47 | 0.24 | 0.94 | 0.46 |
| Q-2 | recovery rate only 71% | | | 1.97 | 15.8 | 6.0 | 14.8 | 17.1 | 1.45 | 0.23 | 0.98 | 0.48 |
| R-1 | 234 | 39 | 2701 | 1.92 | 17.2 | 6.6 | 19.1 | 8.2 | 1.49 | 0.24 | 1.19 | 0.22 |
| R-2 | 143 | 25 | 2280 | 1.81 | 16.9 | 6.4 | 19.0 | 8.7 | 1.47 | 0.23 | 1.19 | 0.23 |

*viscosity measured as a 2.0 wt % solution of the esterified cellulose ether in 0.43 wt % aqueous NaOH at 20° C.
[1] Comparative Example A: HPMC of 6 mPa·s
[2] Comparative Example B: HPMC of 3 mPa·s The results in Table 2 above illustrate that the esterified cellulose ethers of the present invention have a significantly higher [Wf(>100 k)−Wf(>100 k)XL]/WF(>100 k)XL than the esterified cellulose ethers of the prior art. This means that the contributions from chain association and/or aggregation, relative to the contributions from chain cross-linking, in the high molecular weight fraction of the molecular weight distribution is higher in the esterified cellulose ethers of the present invention than in the esterified cellulose ethers of the prior art.

In the HPLC method utilized for determination of $M_w$, $M_n$ and $M_z$, in all Examples 1-8 and in Comparative Examples A to P a sufficiently recovery rate (=[weight of HPMCAS recovered from HPLC column/weight of HPMCAS introduced into HPLC column]×100) was achieved to allow a reliable determination of $M_w$, $M_n$ and M. However, in Comparative Examples Q-1 and Q-2 the recovery rate was too low to make a reasonably reliable $M_w$, $M_n$ and $M_z$ determination.

In the above-described method for the determination of Wf(>100 k) and Wf(>100 k)XL the achieved recovery rate was not sufficient for any of the Comparative Examples P, Q-1, Q-2, R-1 and R-2 to enable a reasonably reliable Wf(>100 k) and Wf(>100 k)XL determination.

The invention claimed is:

1. A partially cross-linked esterified cellulose ether having
   A) groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation, and
   B) having a molecular weight distribution such that [Wf(>100 k)−Wf(>100 k)XL]/Wf(>100 k)XL is at least 0.20,
   wherein Wf(>100 k) is the total weight fraction of the esterified cellulose ether that exceeds 100,000 g/mol, and Wf(>100 k)XL is the weight fraction that exceeds 100,000 g/mol of the esterified cellulose ether that has been subjected to methylation after production of the esterified cellulose ether
   wherein Wf(>100 k) and Wf(>100 k)XL are determined by Size Exclusion Chromatography using tetrahydrofuran as eluent and polystyrene calibration standards.

2. The esterified cellulose ether of claim 1 wherein the groups of the formula —C(O)—R—COOA are —C(O)—$CH_2$—$CH_2$—COOA, —C(O)—CH═CH—COOA, or —C(O)—$C_6H_4$—COOA and the aliphatic monovalent acyl groups are acetyl, propionyl or butyryl groups.

3. The esterified cellulose ether of claim 1 being hydroxypropyl methyl cellulose acetate succinate.

4. The esterified cellulose ether of claim 1 having a viscosity of up to 4.0 mPa·s, measured as a 2.0 wt % solution of the esterified cellulose ether in 0.43 wt % aqueous NaOH at 20° C.

5. The esterified cellulose ether of claim 1 wherein [Wf(>100 k)−Wf(>100 k)XL]/Wf(>100 k)XL is from 0.22 to 3.0.

6. The esterified cellulose ether of claim 1 having a weight average molecular weight Mw of from 80,000 Dalton to 350,000 Dalton, measured by SEC-MALLS using as mobile phase a mixture of 40 parts by volume of acetonitrile and 60 parts by volume of aqueous buffer containing 50 mM $NaH_2PO_4$ and 0.1 M $NaNO_3$.

7. A composition comprising a liquid diluent and at least one esterified cellulose ether of claim 1.

8. The composition of claim 7 additionally comprising at least one active ingredient and optionally one or more adjuvants.

9. A solid dispersion comprising at least one active ingredient in at least one esterified cellulose ether of claim 1.

10. The solid dispersion of claim 9 in the form of strands, pellets, granules, pills, tablets, caplets, microparticles, fillings of capsules or injection molded capsules or in the form of a powder, film, paste, cream, suspension or slurry.

11. A process for producing the solid dispersion of claim 9 comprising the steps of blending a) at least one esterified cellulose ether of claim 1, b) one or more active ingredients and c) one or more optional additives, and subjecting the blend to extrusion.

12. A process for producing the solid dispersion of claim 9 comprising the steps of blending a) at least one esterified cellulose ether of claim 1, b) one or more active ingredients, c) one or more optional additives, and d) a liquid diluent to prepare a liquid composition, and removing said liquid diluent.

13. The process of claim 12 wherein the liquid composition is subjected to spray-drying.

14. A dosage form being coated with the esterified cellulose ether of claim 1.

15. A capsule shell comprising the esterified cellulose ether of claim 1.

* * * * *